United States Patent

Myers et al.

Patent Number: 5,266,303

Date of Patent: Nov. 30, 1993

[54] AEROSOL HAIR SPRAY FORMULATIONS

[75] Inventors: Garry L. Myers; John J. Hiller, both of Kingsport; Robin L. Minga, Blountville; Suzanne W. Dobbs; Andy H. Singleton, both of Kingsport, all of Tenn.

[73] Assignee: Eastman Kodak Company, Rochester, N.Y.

[21] Appl. No.: 983,337

[22] Filed: Nov. 30, 1992

[51] Int. Cl.$^5$ ............................................. A61K 9/12
[52] U.S. Cl. ............................................. 424/47; 424/45; 424/DIG. 1; 424/70; 424/71
[58] Field of Search ............... 424/45, 43, 47, DIG. 1, 424/70, 71, 78.08; 523/501; 524/427, 501, 601

[56] References Cited

U.S. PATENT DOCUMENTS

| | | | |
|---|---|---|---|
| 4,150,216 | 4/1979 | Quack | 528/290 |
| 4,223,009 | 9/1980 | Chakrabarti | 424/DIG. 1 |
| 4,300,580 | 11/1981 | O'Neill | 132/7 |
| 4,536,390 | 8/1985 | Padden | 424/DIG. 1 |
| 5,176,898 | 1/1993 | Goldberg | 424/71 |

*Primary Examiner*—Thurman K. Page
*Assistant Examiner*—G. S. Kishore
*Attorney, Agent, or Firm*—John D. Thallemer; William P. Heath, Jr.

[57] ABSTRACT

This invention relates to aerosol hair spray formulations based on (1) a sulfonate-containing, water-dispersible or water-dissipatible, linear polyester having a glass transition temperature of about 36° C. to about 40° C. and (2) a water-soluble, polyvinyl lactam polymer. In addition, the formulations contain water as the liquid vehicle and a propellant. Such aerosol hair spray formulations do not contain any volatile organic compounds other than propellant yet exhibit fast drying times and excellent performance characteristics.

14 Claims, No Drawings

AEROSOL HAIR SPRAY FORMULATIONS

FIELD OF THE INVENTION

This invention relates to aerosol hair spray formulations based on (1) a sulfonate containing, water dispersible or water dissipatible, linear polyester having a glass transition temperature of about 36° C. to about 40° C. and (2) a water soluble, polyvinyl lactam polymer. In addition, the formulations contain water as the liquid vehicle and a propellant. Such aerosol hair spray formulations do not contain any volatile organic compounds other than propellant yet exhibit fast drying times and excellent performance characteristics.

BACKGROUND OF THE INVENTION

Hair spray formulations typically comprise a solution of a polymer, the fixative, in water/alcohol mixtures. The polymeric materials which are typically used in hair spray formulations are soluble in water or water/alcohol mixtures and are derived from N-vinyl-pyrrolidinone or N-vinylpyrrolidinone and one or more other vinyl monomers such as vinyl acetate, acrylate and methacrylate esters and/or styrene compounds. When applied to hair and allowed to dry, the polymeric material provides human hair body, consistency, firm texture, and, in general, maintains the hair in a desired arrangement.

Significant amounts of volatile organic compounds such as alcohols are present in such hair spray formulations to facilitate rapid drying of the polymer solution. Environmental concerns continue to encourage the development of hair spray formulations which contain very little and preferably no volatile organic compounds. Attempts to omit the volatile organic component of hair sprays have failed to produce formulations which have acceptable drying times, particularly when the water level exceeds about 55% by weight of the formulation.

U.S. Pat. No. 4,300,580 describes hair spray formulations containing a water-dispersible or water-dissipatible linear sulfo-polyester fixative in a water/alcohol mixture. Such formulations are fast drying and have good hair holding properties but possess the disadvantage of being very difficult to remove from the hair. For example, prolonged washing is required to completely remove the water dispersible, linear polyester fixative to obtain hair with no tacky or sticky feel. In an effort to overcome the fixative removal problem, U.S. Pat. No. 4,300,580 teaches the addition of certain water soluble polymers to formulations containing the water-dispersible, linear polyester. The use of poly(alkylene glycols) such as poly(ethylene glycol) is disclosed. However, when such formulations containing a combination of the poly(alkylene glycol) and water dispersible, linear polyester are applied to hair and allowed to dry, the fixative causes a matting of the hair. Such matting hinders combing, brushing and styling of hair. It is important to note that U.S. Pat. No. 4,300,580 recommends in column 4, lines 36-38, a "nonaerosol" method of application of the hair spray formulation.

U.S. Pat. No. 4,150,216 discloses grooming formulations containing branched sulfo-polyesters. Difficulty, however, is encountered in maintaining the specified molecular weight range of 600 to 5,000. Slight variations in the condensation temperatures and/or times results in branched polymers having molecular weights which exceed the desired values and which have poor film forming characteristics, i.e. they are hard and brittle, and are not readily water dispersible or soluble as required in hair spray formulations.

Copending commonly assigned U.S. patent application Ser. No. 07/892,297 discloses water based, film forming formulations which contain as the fixative a combination of (1) a sulfonate containing, water-dispersible or water-dissipatible, linear polyester and (2) a water-soluble, polyvinyl lactam polymer. While the glass transition temperature (Tg) of the polyester is not specified, the application lists commercially available polyesters which have a Tg of from 29° C. to 55° C.

The present inventors have unexpectedly discovered that aerosol hair spray formulations wherein the fixative is a combination of two polymeric materials: (1) a sulfonate containing, water dissipatible, linear polyester having a Tg of about 36° C. to about 40° C. and (2) a water soluble, poly-vinyl lactam polymer, exhibit improved properties over aerosol hair sprays containing a sulfopolyester having a Tg outside of said range. The aerosol hair spray formulations of the present invention do not have the disadvantages described hereinabove, such as tackiness, matting and difficulty in removal. Moreover, the aerosol hair spray formulations do not contain any volatile organic compounds other than propellant.

SUMMARY OF THE INVENTION

Accordingly, it is one object of the present invention to provide an aerosol hair spray formulation having improvements in one or more of the above desirable features.

Accordingly, it is another object of the invention to provide an aerosol hair spray formulation which is not tacky, has a fast drying rate, acceptable body, consistency and firm texture necessary to hold hair in the desired arrangement for a certain length of time and does not contain any volatile organic compounds.

Still another object of the invention is to provide an aerosol hair spray formulation having excellent storage stability and which does not clog or produce foam at the exit port of an aerosol container.

These and other objects are accomplished herein by an aerosol hair spray composition comprising:

(1) about 1 to about 10 weight percent based on the weight of components (1), (2), (3) and (4) of a sulfopolyester having a glass transition temperature of 36° C. to 40° C. consisting essentially of repeat units from (a) a dicarboxylic acid selected from the group consisting of aromatic dicarboxylic acids, saturated aliphatic dicarboxylic acids, cycloaliphatic dicarboxylic acids, and combinations thereof;

(b) a diol; and (c) a difunctional sulfomonomer containing at least one sulfonate group attached to an aromatic nucleus wherein the functional groups are hydroxy, carboxy or amino, provided the difunctional sulfomonomer is present in an amount from 4 to 25 mole percent based on 100 mole percent dicarboxylic acid and 100 mole percent diol; and (2) about 1 to about 7 weight percent based on the weight of components (1), (2), (3) and (4) of a water-soluble, polyvinyl lactam polymer containing at least 50 mole percent of residues of N-vinyl lactams of the formula

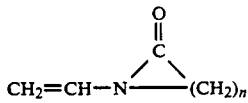

wherein n is 3 or 4;

(3) about 46 to about 94 weight percent based on the weight of components (1), (2), (3) and (4) of a liquid vehicle consisting essentially of water; and (4) about 3 to about 40 weight percent based on the weight of components (1), (2), (3) and (4) of a propellant selected from the group consisting of a $C_1$–$C_4$ aliphatic hydrocarbon, dimethyl ether, and mixtures thereof.

DESCRIPTION OF THE INVENTION

The term "hair" as used in the present invention includes treated and untreated human hair, animal hair, and any type of fiber which requires consistency and firm texture necessary to hold it in the desired arrangement for a certain length of time.

The sulfo polyester, component (1), has a glass transition temperature in the critical range of about 36° C. to about 40° C. and contains repeat units from a dicarboxylic acid, a diol and a difunctional sulfomonomer. Dicarboxylic acids useful in the present invention include aromatic dicarboxylic acids preferably having 8 to 14 carbon atoms, saturated aliphatic dicarboxylic acids preferably having 4 to 12 carbon atoms, and cycloaliphatic dicarboxylic acids preferably having 8 to 12 carbon atoms. Specific examples of dicarboxylic acids are: terephthalic acid, phthalic acid, isophthalic acid, naphthalene-2,6-dicarboxylic acid, cyclohexanedicarboxylic acid, cyclohexanediacetic acid, diphenyl-4,4'-dicarboxylic acid, succinic acid, glutaric acid, adipic acid, azelaic acid, sebacic acid, and the like. The polyester may be prepared from two or more of the above dicarboxylic acids.

It should be understood that use of the corresponding acid anhydrides, esters, and acid chlorides of these acids is included in the term "dicarboxylic acid".

The diol component of the polyester includes cycloaliphatic diols preferably having 6 to 20 carbon atoms or aliphatic diols preferably having 3 to 20 carbon atoms. Examples of such diols are: ethylene glycol, diethylene glycol, triethylene glycol, 1,4-cyclohexanedimethanol, propane-1,3-diol, butane-1,4-diol, pentane-1,5-diol, hexane-1,6-diol 3-methylpentanediol-(2,4), 2-methylpentanediol-(1,4), 2,2,4-trimethylpentane-diol-(1,3), 2-ethylhexanediol-(1,3), 2,2-diethylpropane-diol-(1,3), hexanediol-(1,3), 1,4-di-(hydroxyethoxy)-benzene, 2,2-bis-(4-hydroxycyclohexyl)-propane, 2,4-dihydroxy-1,1,3,3-tetramethyl-cyclobutane, 2,2-bis-(3-hydroxyethoxyphenyl)-propane, and 2,2-bis-(4-hydroxypropoxyphenyl)-propane. The polyester may be prepared from two or more of the above diols.

The difunctional sulfomonomer component of the polyester may be a dicarboxylic acid or an ester thereof containing a sulfonate group ($-SO_3^{31}$), a diol containing a sulfonate group, or a hydroxy acid containing a sulfonate group. The cation of the sulfonate salt may be Na+, Li+, K+, NH$_4$+, and substituted ammonium. The term "substituted ammonium" refers to ammonium substituted with an alkyl or hydroxy alkyl radical having 1 to 4 carbon atoms. The difunctional sulfomonomer contains at least one sulfonate group attached to an aromatic nucleus wherein the functional groups are hydroxy, carboxy or amino. Advantageous difunctional sulfomonomer components are those wherein the sulfonate salt group is attached to an aromatic acid nucleus such as benzene, naphthalene, diphenyl, oxydiphenyl, sulfonyldiphenyl or methylenediphenyl nucleus. Preferred results are obtained through the use of sulfophthalic acid, sulfoterephthalic acid, sulfoisophthalic acid, 4-sulfonaphthalene-2,7-dicarboxylic acid, and their esters. The sulfomonomer is present in an amount from 4 to 25 mole percent, preferably 10 to 12 mole percent, based on 100 mole percent dicarboxylic acid and 100 mole percent diol.

In particularly preferred embodiments, the water dispersible sulfo-containing linear polyester is derived from (a) a mixture of dicarboxylic acids consisting of isophthalic acid (or ester) and 5-sodio-sulfoisophthalic acid, (b) a diol component consisting of diethylene glycol, or a mixture of diols consisting of at least 75 mole percent of diethylene glycol with the remaining diol being either ethylene glycol or 1,4-cyclohexanedimethanol. The sulfo-polyester, component (1), is present in an amount of about 1 to about 10 weight percent, based on the weights of components (1), (2), (3) and (4) of the aerosol hair spray formulation.

Component (2) is a water soluble vinyl polymer or copolymer which contains at least 50 mole percent of the residues of n-vinyl lactam monomer the formula

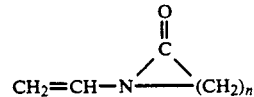

In the above formula, n is 3 or 4. Preferably, n equals three wherein the N-vinyl lactam monomer is N-vinylpyrrolidinone. Examples of other vinyl compounds which may be copolymerized with an N-vinyl lactam to prepare the water soluble polymers include vinyl esters and vinyl aromatic compounds having the structure

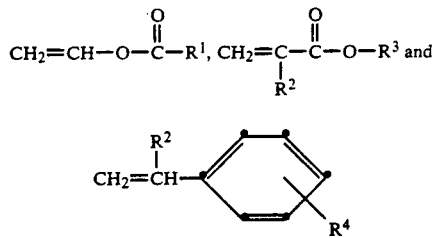

wherein $R^1$ is alkyl, e.g., straight-and branched-chain alkyl of up to about 10 carbon atoms; $R^2$ is hydrogen or methyl; $R^3$ is alkyl, e.g., straight-and branched-chain alkyl of up to about 10 carbon atoms, and alkyl substituted by hydroxy or by amino including alkylamino and dialkylamino; and $R^4$ is hydrogen or alkyl of up to about 4 carbon atoms.

The water soluble polymers, component (2), may be prepared according to known procedures wherein a N-vinyl lactam is polymerized, optionally in the presence of one or more other vinyl monomers such as those described above. The N-vinylpyrrolidinone/vinyl acetate copolymers supplied by BASF under the tradename Luviskol VA are typical of the water-soluble polymers which may be used in the aerosol hair spray compositions of the present invention. The preferred water soluble polymers comprise homopolymers of N-vinyl-2-pyrrolidinone and copolymers of N-vinyl-2- pyrrolidinone and up to 50 mole percent vinyl acetate having weight average molecular weights in the range of about 1000 to 100,000. The water-soluble, poly-vinyl lactam polymer, component (2), is present in an amount of about 1 to about 7 weight percent, based on the weights of components (1), (2), (3) and (4) of the aerosol hair spray formulation.

Component (3) of the aerosol hair spray formulations is a liquid vehicle. The liquid vehicle of the formulations may be water or a water/alcohol mixture. Distilled or deionized water are the preferred sources of water since tap water generally contains ions which would precipitate the sulfopolyester, component (1). The alcohol should have two to four carbon atoms. Specific alcohols include, ethanol, isopropanol and t-butanol. A preferred water/alcohol mixture contains 55 to 65 weight percent water and 35 to 45 weight percent alcohol. The preferred alcohol is ethanol. The liquid vehicle is present in an amount of about 46 to about 94 weight percent, based on the weights of components (1), (2), (3) and (4) of the aerosol hair spray formulation.

Component 4 is a propellant selected from the group consisting of a $C_1$-$C_4$ aliphatic hydrocarbons and dimethyl ether. The aliphatic hydrocarbons may be branched or straight chain and include methane, ethane, propane, n-butane, isobutane, or mixtures thereof. A preferred aliphatic hydrocarbon propellant is a mixture containing about 83 percent isobutane and about 17 percent propane. The propellant is present in an amount of about 3 to about 40 weight percent, based on the weights of components (1), (2), (3) and (4) of the aerosol hair spray formulation. In the case where a $C_1$-$C_4$ aliphatic hydrocarbon is used as the propellant, generally about 3 to about 10 weight percent, preferably 4 to 7 weight percent, is employed. In the case where dimethyl ether is used as the propellant, generally, about 30 to about 40 weight percent, preferably, 30 to 35 weight percent, is employed.

Other conventional additives such as preservatives, fragrances, antifoaming agents, hair conditioners, plasticizers, etc. may be added in such quantities as desired, up to about 5.0% by weight of the total formulation. Although the film forming formulations described herein are particularly useful as aerosol hair sprays for the grooming of hair, it is possible that the formulations, with or without modification, may be used in other types of personal care products.

It is unexpected, based on the prior art, that the combination of a sulfo-containing water dispersible polyester having a Tg of 36° C. to 40° C. with a water soluble vinyl polymer would give aerosol hair spray formulation improvements over either of the single component systems or a dual component system at other glass transition temperatures, particularly in washability/rinsability, tackiness, humidity resistance and film elasticity.

The materials and testing procedures used for the results shown herein are as follows:

DYMEL A (CTFA Adopted Name: Dimethyl Ether) available from DuPont, is a dimethyl ether and is used as a propellant.

LUVISKOL VA 73W PVP/VA (CTFA Adopted Name: PVP/VA Copolymer), available from BASF, is a water soluble vinyl copolymer of 70 mole percent of N-vinyl-2-pyrrolidinone and 30 mole percent of vinyl acetate (50% solids), and is used as a fixative.

GLYDANT (CTFA Adopted Name: DMDM Hydantoin) available from Lonza, Inc. is 1-(hydroxymethyl)-5,5-dimethyl hydantoin, and is used as a antimicrobial.

Inherent viscosity (I.V.) was measured at 23° C. using 0.50 grams of polymer per 100 ml of a solvent consisting of 60% by weight phenol and 40% by weight tetrachloroethane.

Preparation of tresses involved natural brown, European virgin hair. About two grams of hair, root end, were glued to a 2" by 2" plastic tab. The tresses were cut so that the length of hair hanging below the tabs was six inches.

The invention will be further illustrated by a consideration of the following examples, which are intended to be exemplary of the invention. All parts and percentages in the examples are on a weight basis unless otherwise stated.

EXAMPLE I

Preparation of a water-dispersible sulfo-polyester

A 500 mL round bottom flask equipped with a ground-glass head, an agitator shaft, nitrogen inlet and a side arm was charged with 74.0 grams of isophthalic acid, 16.0 grams of 5-sodiosulfoisophthalic acid, 106.0 grams of diethylene glycol, sufficient titanium isopropoxide to provide 50 ppm of titanium, and 0.45 grams of sodium acetate tetrahydrate. The flask was immersed in a Belmont bath at 200° C. for two hours under a nitrogen sweep. The temperature of the bath was increased to 280° C. and the flask was heated for one hour under reduced pressure of 0.5 to 0.1 mm of Hg. The flask was allowed to cool to room temperature and the copolyester was removed from the flask. The copolyester had an I.V. of about 0.45 and a glass transition temperature of about 30° C. as measured using a differential scanning calorimeter (DSC). The copolyester was extruded and pelletized.

EXAMPLE II

Preparation of an aerosol hair spray formulation

The copolyester prepared in Example I, 7.14 grams, was dispersed in 52.15 grams of distilled water by heating and stirring until a temperature of about 85° C. was reached. After cooling to 40° C. any water lost during heating was replaced and 5.71 grams of a water soluble vinyl copolymer consisting of 70 mole percent of N-vinyl-2-pyrrolidinone and 30 mole percent of vinyl acetate (50% solids) was added at 40° C. The mixture was stirred and filtered to remove any residual material. The pH was adjusted to 5.5±0.5 followed by the addition of 35.0 grams of ethanol.

To 61.88 grams of the composition was added 15.4 grams of a mixture containing about 83 percent isobutane and about 17 percent propane. The formulation was applied in the form of an aerosol hair spray to hair tresses. The test results are summarized in Table I.

EXAMPLE III

Preparation of a water-dispersible sulfo-polyester

A 500 mL round bottom flask equipped with a ground-glass head, an agitator shaft, nitrogen inlet and a side arm was charged with 74.0 grams of isophthalic acid, 16.0 grams of 5-sodiosulfoisophthalic acid, 83.0 grams of diethylene glycol, 16.0 grams of 1,4-cyclohexanedimethanol, sufficient titanium isopropoxide to provide 50 ppm of titanium, and 0.45 grams of sodium acetate tetrahydrate. The flask was immersed in a Belmont bath at 200° C. for one hour under a nitrogen sweep. The temperature of the bath was increased to 230° C. for one hour. The temperature of the bath was increased to 280° C. and the flask was heated for 45 minutes under reduced pressure of 0.5 to 0.1 mm of Hg. The flask was allowed to cool to room temperature and the copolyester was removed from the flask. The copolyester had an I.V. of about 0.36 and a glass transition temperature of about 38° C. as measured using a differential scanning calorimeter (DSC). The copolyester was extruded and pelletized.

EXAMPLE IV

Preparation of an aerosol hair spray formulation

The copolyester prepared in Example III, 17.85 grams, was dispersed in 217.9 grams of distilled water by heating and stirring at 80–85° C. for 15 minutes. The mixture was cooled to 40° C. Water lost during heating was replaced by adding distilled water. A water soluble vinyl copolymer consisting of 70 mole percent of N-vinyl-2-pyrrolidinone and 30 mole percent of vinyl acetate (50% solids), 14.3 grams, was added and the mixture was stirred and filtered to remove residual material The pH was adjusted to 5.5±0.5 and 0.2 weight percent of 1-(hydroxymethyl)-5,5-dimethyl hydantoin was added. Good storage stability of the formulation was observed after aging at 40° C. for one week in an oven.

To 70.0 grams of the above hair spray formulation was added 30.0 grams of dimethyl ether. The all aqueous aerosol formulation showed good clarity and storage stability. The formulation was applied in the form of an aerosol hair spray to hair tresses. The test results are summarized in Table I.

EXAMPLE V

Preparation of an aerosol hair spray formulation

The copolyester prepared in Example III, 7.14 grams, was dispersed in 52.15 grams of distilled water by heating and stirring until a temperature of about 85° C. was reached. After cooling to 40° C. any water lost during heating was replaced and 5.71 grams of a water soluble vinyl copolymer consisting of 70 mole percent of N-vinyl-2-pyrrolidinone and 30 mole percent of vinyl acetate (50% solids) was added at 40° C. The mixture was stirred and filtered to remove any residual material. The pH was adjusted to 5.5±0.5 followed by the addition of 35.0 grams of ethanol.

To 61.88 grams of the composition was added 15.4 grams of a mixture containing about 83 percent isobutane and about 17 percent propane. The formulation was applied in the form of an aerosol hair spray to hair tresses. The test results are summarized in Table I.

EXAMPLE VI

Preparation of a water-dispersible sulfo-polyester

A 500 mL round bottom flask equipped with a ground-glass head, an agitator shaft, nitrogen inlet and a side arm was charged with 136.0 grams of isophthalic acid, 53.0 grams of 5-sodiosulfoisophthalic acid, 155.0 grams of diethylene glycol, 78.0 grams of 1,4-cyclohexanedimethanol, sufficient titanium isopropoxide to provide 50 ppm of titanium, and 1.48 grams of sodium acetate tetrahydrate. The flask was immersed in a Belmont bath at 200° C. for one hour under a nitrogen sweep. The temperature of the bath was increased to 230° C. for one hour. The temperature of the bath was increased to 280° C. and the flask was heated for 45 minutes under reduced pressure of 0.5 to 0.1 mm of Hg. The flask was allowed to cool to room temperature and the copolyester was removed from the flask. The copolyester had an I.V. of about 0.33 and a glass transition temperature of about 55° C. as measured using a differential scanning calorimeter (DSC). The copolyester was extruded and pelletized.

EXAMPLE VII

Preparation of an aerosol hair spray formulation

The copolyester prepared in Example VI, 17.85 grams, was dispersed in 217.9 grams of distilled water by heating and stirring at 80–85° C. for 15 minutes. The mixture was cooled to 40° C. Water lost during heating was replaced by adding distilled water. A water soluble vinyl copolymer consisting of 70 mole percent of N-vinyl-2-pyrrolidinone and 30 mole percent of vinyl acetate (50% solids), 14.3 grams, was added and the mixture was stirred and filtered to remove residual material The pH was adjusted to 5.5±0.5 and 0.2 weight percent of 1-(hydroxymethyl)-5,5-dimethyl hydantoin was added. Good storage stability of the formulation was observed after aging at 40° C. for one week in an oven.

To 70.0 grams of the above hair spray formulation was added 30.0 grams of dimethyl ether. The sulfo polyester precipitated. Dimethyl ether was replaced with ethane and the sulfo-polyester precipitated. Thus, the sulfo polyester having a Tg of about 55° C. was not compatible with any of the propellants which are necessary in aerosol hair spray formulations.

EXAMPLE VIII

In order to evaluate the effect of the glass transition temperature of the linear sulfo-polyester in a aerosol hair spray formulation, tresses were treated with the aerosol hair spray formulations of Examples II and V. The aerosol hair spray formulation of Example II contains a sulfo-polyester having a Tg of about 30° C. while the aerosol hair spray formulation of Example V contains a sulfo-polyester having a Tg of about 38° C. Other than the glass transition temperature, the formulations were essentially identical. One tress per treatment was used. The tresses were sprayed with the respective aerosol hair spray for 10 seconds each which was enough time to completely cover each of the tresses. Individual tresses were dried under heat while subjective feel tests were conducted on the wet tresses. The subjective evaluations were conducted by a panel of ten people. The evaluators rated the tresses on a scale of 1 to 10. The lower values indicate hair that was more tacky or sticky when touched. The average of these results by each evaluator for each of the aerosol hair sprays are summarized in Table I.

TABLE I

| Effect of Tg in Aerosol Hair Spray Formulations | | |
|---|---|---|
| | Subjective Evaluations | |
| Evaluator | 30° C. Tg Hair Spray | 38° C. Tg Hair Spray |
| A | 4.0 | 8.5 |
| B | 3.0 | 9.0 |
| C | 3.0 | 8.0 |
| D | 3.5 | 8.0 |
| E | 4.5 | 8.5 |
| F | 4.0 | 8.0 |
| G | 2.5 | 9.0 |

TABLE I-continued

| Effect of Tg in Aerosol Hair Spray Formulations | | |
|---|---|---|
| | Subjective Evaluations | |
| Evaluator | 30° C. Tg Hair Spray | 38° C. Tg Hair Spray |
| H | 3.0 | 7.0 |
| I | 4.0 | 8.0 |
| J | 3.5 | 9.0 |
| AVERAGE | 3.5 | 8.3 |

The results in Table I clearly indicate that the aerosol hair spray formulation containing the sulfo-polyester having a Tg of about 38° C. proved to be significantly superior in terms of being less tacky or sticky than the hair spray formulation containing the sulfo-polyester having a Tg of about 30° C. The average values of 3.5 and 8.3 on the scale of 1 to 10 indicates a significant deviation in tacky or sticky feel to hair treated with the different aerosol hair spray formulations. In addition, the hair spray formulation containing the sulfo polyester having a Tg of about 38° C. had good rinsability/washability and humidity resistance.

Many variations will suggest themselves to those skilled in this art in light of the above detailed description. All such obvious modifications are within the full intended scope of the appended claims.

What is claimed is:

1. An aerosol hair spray formulation comprising:
   (1) a linear sulfo-polyester having a glass transition temperature of about 36° C. to about 40° C. consisting essentially of repeat units from
      (a) a dicarboxylic acid selected from the group consisting of aromatic dicarboxylic acids, saturated aliphatic dicarboxylic acids, cycloaliphatic dicarboxylic acids, and combinations thereof;
      (b) a diol; and
      (c) a difunctional sulfomonomer containing at least one sulfonate group attached to an aromatic nucleus wherein the functional groups are hydroxy, carboxy or amino, provided the difunctional sulfomonomer is present in an amount from 4 to 25 mole percent based on 100 mole percent dicarboxylic acid and 100 mole percent diol; and
   (2) a water-soluble, poly-vinyl lactam polymer containing at least 50 mole percent of residues of N-vinyl lactams of the formula

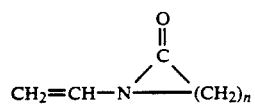

wherein n is 3 or 4;
   (3) a liquid vehicle consisting essentially of water; and
   (4) a propellant selected from the group consisting of a $C_1$-$C_4$ aliphatic hydrocarbon, dimethyl ether, and mixtures thereof.

2. An aerosol hair spray formulation comprising:
   (1) about 1 to about 10 weight percent based on the weight of components (1), (2), (3) and (4) of a sulfo-polyester having a glass transition temperature of 36° C. to 40° C. consisting essentially of repeat units from
      (a) a dicarboxylic acid selected from the group consisting of aromatic dicarboxylic acids, saturated aliphatic dicarboxylic acids, cycloaliphatic dicarboxylic acids, and combinations thereof;
      (b) a diol; and
      (c) a difunctional sulfomonomer containing at least one sulfonate group attached to an aromatic nucleus wherein the functional groups are hydroxy, carboxy or amino, provided the difunctional sulfomonomer is present in an amount from 4 to 25 mole percent based on 100 mole percent dicarboxylic acid and 100 mole percent diol; and
   (2) about 1 to about 7 weight percent based on the weight of components (1), (2), (3) and (4) of a water-soluble, polyvinyl lactam polymer containing at least 50 mole percent of residues of N-vinyl lactams of the formula

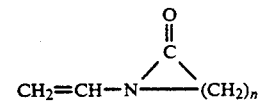

wherein n is 3 or 4;
   (3) about 46 to about 94 weight percent based on the weight of components (1), (2), (3) and (4) of a liquid vehicle consisting essentially of water; and
   (4) about 3 to about 40 weight percent based on the weight of components (1), (2), (3) and (4) of a propellant selected from the group consisting of a $C_1$-$C_4$ aliphatic hydrocarbon, dimethyl ether, and mixtures thereof.

3. An aerosol hair spray formulation comprising:
   (1) 3 to 7 weight percent based on the weight of components (1), (2), (3) and (4) of a sulfo-polyester having a glass transition temperature of 36° C. to 40° C. consisting essentially of repeat units from
      (a) a dicarboxylic acid selected from the group consisting of aromatic dicarboxylic acids, saturated aliphatic dicarboxylic acids, cycloaliphatic dicarboxylic acids, and combinations thereof;
      (b) a diol; and
      (c) a difunctional sulfomonomer containing at least one sulfonate group attached to an aromatic nucleus wherein the functional groups are hydroxy, carboxy or amino, provided the difunctional sulfomonomer is present in an amount from 4 to 25 mole percent based on 100 mole percent dicarboxylic acid and 100 mole percent diol; and
   (2) 1 to 4 weight percent based on the weight of components (1), (2), (3) and (4) of a water-soluble, polyvinyl lactam polymer containing at least 50 mole percent of residues of N-vinyl lactams of the formula

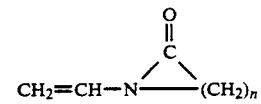

wherein n is 3 or 4;
   (3) 55 to 70 weight percent based on the weight of components (1), (2), (3) and (4) of a liquid vehicle consisting essentially of distilled or deionized water; and
   (4) 30 to 40 weight percent based on the weight of components (1), (2), (3) and (4) of a dimethyl ether propellant.

4. The aerosol hair spray formulation of claim 1 wherein the dicarboxylic acid component is selected from the group consisting of terephthalic acid, phthalic acid, isophthalic acid, naphthalene 2,6-dicarboxylic acid, cyclohexanedicarboxylic acid, cyclohexanediacetic acid, and mixtures thereof.

5. The aerosol hair spray formulation of claim 4 wherein the dicarboxylic acid component is isophthalic acid.

6. The aerosol hair spray formulation of claim 1 wherein the diol component is selected from the group consisting of ethylene glycol, diethylene glycol, triethylene glycol, 1,4-cyclohexanedimethanol, and mixtures thereof.

7. The aerosol hair spray formulation of claim 6 wherein the diol component is a mixture of diethylene glycol and 1,4-cyclohexanedimethanol.

8. The aerosol hair spray formulation of claim 1 wherein the difunctional sulfomonomer component is selected from the group consisting of sulfophthalic acid, sulfoterephthalic acid, sulfoisophthalic acid, 4-sulfonaphthalene-2,7-dicarboxylic acid, and esters thereof.

9. The aerosol hair spray formulation of claim 8 wherein the difunctional sulfomonomer component is 5-sodio-sulfoisophthalic acid.

10. The aerosol hair spray formulation of claim 1 wherein the sulfo-polyester, component (1), has repeat units from isophthalic acid, diethylene glycol and 1,4-cyclohexanedimethanol, and 5-sodio-sulfoisophthalic acid.

11. The aerosol hair spray formulation of claim 1 wherein the water-soluble, polyvinyl lactam polymer, component (2), contains up to 50 mole percent of residues of vinyl esters and vinyl aromatic compounds selected from the group consisting of

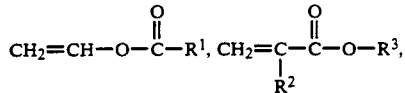

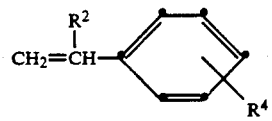

and mixtures thereof, wherein $R^1$ is alkyl; $R^2$ is hydrogen or methyl; $R^3$ is alkyl or alkyl substituted with hydroxy
or amino, alkylamino or dialkylamino; and $R^4$ is hydrogen or alkyl.

12. The aerosol hair spray formulation of claim 1 wherein the propellant, component (4), is a $C_1$-$C_4$ aliphatic hydrocarbon selected from the group consisting of methane, ethane, propane, n-butane, isobutane, and combinations thereof.

13. The aerosol hair spray formulation of claim 12 wherein the propellant, component (4), is a mixture containing about 83 weight percent isobutane and about 17 weight percent propane.

14. The aerosol hair spray formulation of claim 1 which additionally contains an additive selected from the group consisting of preservatives, fragrances, antifoaming agents, hair conditioners and plasticizers.

* * * * *